United States Patent [19]
Aoyama et al.

[11] Patent Number: 5,921,938
[45] Date of Patent: Jul. 13, 1999

[54] SYSTEM AND METHOD FOR ADJUSTING TIME ASSOCIATED WITH MEDICAL EVENT DATA

[75] Inventors: David D. Aoyama, Seattle; Steven B. Duke, Bothell; John Giaever, Seattle, all of Wash.

[73] Assignee: Physio-Control Manufacturing Corporation, Redmond, Wash.

[21] Appl. No.: 08/948,630

[22] Filed: Oct. 9, 1997

[51] Int. Cl.$^6$ .................................................. A61B 5/00
[52] U.S. Cl. ............................... 600/509; 607/5; 128/904
[58] Field of Search ................................. 607/5; 600/300, 600/508, 509; 128/897, 898, 904

[56] References Cited

U.S. PATENT DOCUMENTS

| | | |
|---|---|---|
| 3,862,365 | 1/1975 | Kobayashi et al. . |
| 3,937,004 | 2/1976 | Natori et al. . |
| 3,948,036 | 4/1976 | Morokawa . |
| 4,023,344 | 5/1977 | Mukaiyama . |
| 4,125,993 | 11/1978 | Emile, Jr. . |
| 4,147,022 | 4/1979 | Ichikawa . |
| 4,211,065 | 7/1980 | Schmitz et al. . |
| 4,234,958 | 11/1980 | Pipes et al. . |
| 4,287,597 | 9/1981 | Paynter et al. . |
| 4,501,502 | 2/1985 | Van Orsdel . |
| 4,582,434 | 4/1986 | Plangger et al. . |
| 4,768,178 | 8/1988 | Conklin et al. . |
| 5,274,545 | 12/1993 | Allan et al. . |
| 5,544,661 | 8/1996 | Davis et al. ............................ 128/904 |
| 5,549,115 | 8/1996 | Morgan et al. . |
| 5,593,426 | 1/1997 | Morgan et al. ............................ 607/5 |
| 5,749,902 | 5/1998 | Olson et al. ................................ 607/5 |

FOREIGN PATENT DOCUMENTS

WO 96/10233   4/1996   WIPO .

OTHER PUBLICATIONS

AHA Medical/Scientific Statement, Special Report, Joint Task Force, Recommended Guidelines for Uniform Reporting of Data from Out–of–Hospital Cardiac Arrest: The *Utstein Style,* Circulation, vol. 84, No. 2, Aug. 1991, pp. 960–975.

Early Defibrillation by Police: Initial Experience with Measurement of Critical Time Intervals and Patient Outcome, Roger O. White, MD, Larry F. Vukov, MD and Thomas F. Bugliosi, MD, *Annals of Emergency Medicine,* May 1994, pp. 1009–1013.

(List continued on next page.)

*Primary Examiner*—George Manuel
*Assistant Examiner*—Carl H. Layno
*Attorney, Agent, or Firm*—Christensen O'Connor Johnson & Kindness PLLC

[57] ABSTRACT

A system synchronizes the time of a clock of an electronic physiological instrument with time of a remote time base. The electronic physiological instrument records medical event data and electronically associates event time with the event data While recording, or after recording, the medical event data, the electronic physiological instrument is placed in data communication with the remote time base over a data connection. The remote time base initially determines a reference time from a master clock. The remote time base also transmits a request to the electronic physiological instrument for a current time from a clock in the electronic physiological instrument. If a response is not received from the electronic physiological instrument within a first time period, the clock is not synchronized with the remote time base. If a response is received within the first time period, a time difference is determined between the reference time and the time transmitted from the electronic physiological instrument by subtracting the two times. The time difference is then electronically associated with the medical event data. Associating the time difference with the medical event data allows the time stamps in the event data to be corrected to provide meaningful event reconstruction and analysis independent of any time differences between the two clocks and any time delays incurred in receiving the time from the physiological instrument over the data connection.

26 Claims, 11 Drawing Sheets

OTHER PUBLICATIONS

Does Anybody Really Know What Time It Is? Does Anybody Really Care?, William H. Cordell, MD, FACEP, Michael L. Olinger, MD, FACEP, Paul A. Kozak, MD, Allen W. Nyhuis, MS, *Annals of Emergency Medicine,* May 1994, pp. 1032–1036.

Seiko Receptor Message Watch advertisement. To the best of applicant's knowledge, this advertisement was published more than one year prior to the filing date of the above–identified application.

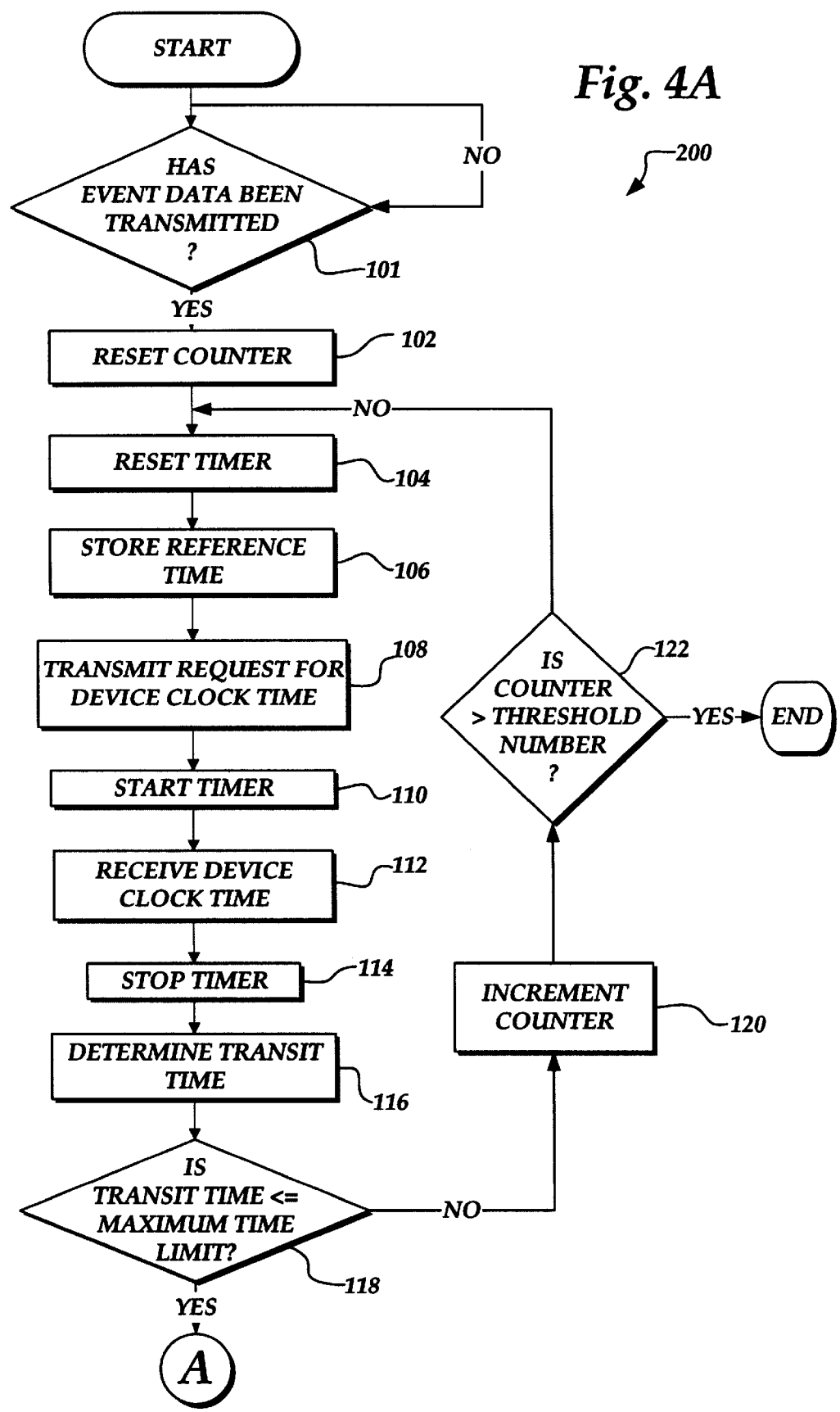

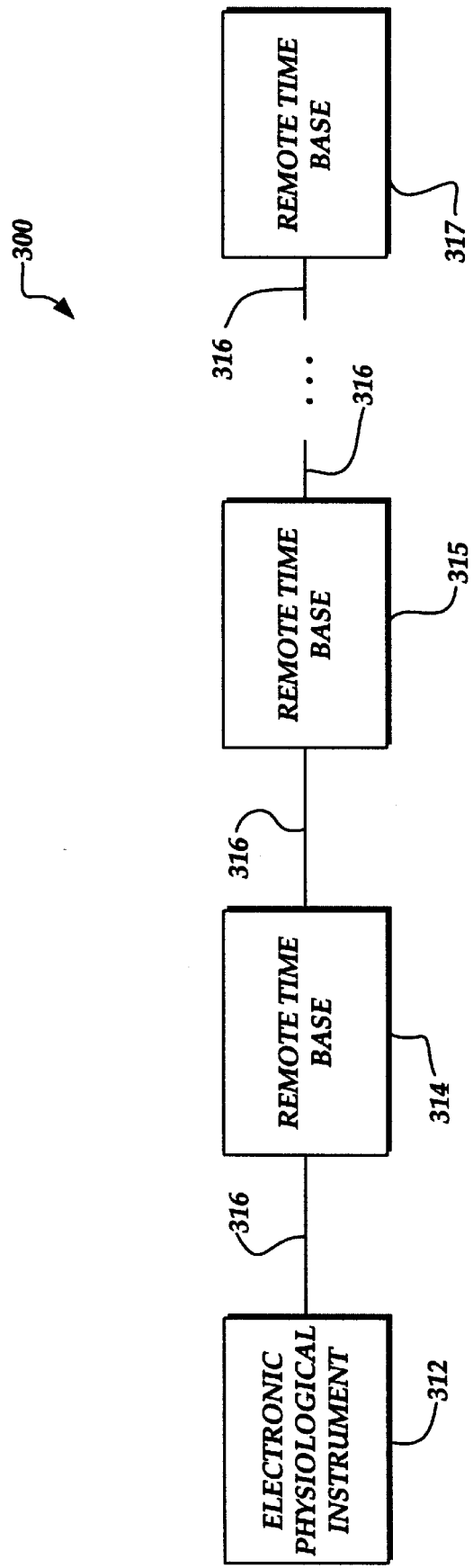

SYSTEM AND METHOD FOR ADJUSTING TIME ASSOCIATED WITH MEDICAL EVENT DATA

This invention generally relates to electronic physiological instruments, and more specifically to a system and method for synchronizing a clock in an electronic physiological instrument.

BACKGROUND OF THE INVENTION

It is well known that the probability of surviving a heart attack depends on the speed with which appropriate medical care is provided. One of the most common and life-threatening consequences of a heart attack is the development of a cardiac arrhythmia such as a ventricular fibrillation, in which the heart is unable to pump a sufficient volume of blood. When such an arrhythmia occurs, serious brain damage and death will invariably result unless a normal heart rhythm can be restored within a few minutes.

The most effective treatment for ventricular fibrillation is the application of a strong electric shock to the victim. The electric shock frequently terminates the chaotic activity characteristic of arrhythmias, and restores the normal pumping action of the heart. Defibrillators for producing and delivering such shocks have been known and successfully used for many years.

An important feature that exists in many portable as well as nonportable defibrillators is the ability to record data surrounding a defibrillation event for later analysis. Most emergency medical organizations have standard protocols that describe how first responders and emergency medical care providers should treat patients during medical emergencies, such as cardiorespiratory emergencies. To assess the effectiveness of these protocols, information about the patient condition and the procedures performed must be collected for post-event review. Event summaries may include patient information, recorded electrocardiograms (ECGs), results of patient assessments, and times of medication and therapy delivery. The data may also include time-coded data corresponding to functions implemented by a defibrillator user, and voice or other data recorded at the site of the emergency. The event data may further include a time index of when the defibrillation pulses were applied to the patient, the energy of each pulse, patient impedance data, and other patient and system events necessary to reconstruct the defibrillation therapy. All event data are preferably associated with time stamps so that an accurate timeline can later be reconstructed for analysis.

A typical method of accessing the stored data is to later download it through a dedicated data port located on the defibrillator. To download the data using known methods, a communication cable is connected between the dedicated data port on the defibrillator and a communication port on a computer. Data surrounding the defibrillation event is then downloaded to the computer where it may be stored for later analysis.

Accurate time stamps on the recorded event data are desirable in order to ensure that event reconstruction and analysis are meaningful. Inaccurate time stamps can result from the internal clock of the defibrillator being out of synchronization with a reference time base maintained by the emergency medical system. Event data that is recorded by a defibrillator having an internal clock out of synchronization with the reference clock that is later used for event reconstruction can yield incongruous results. An example of an incongruous result is a time stamp indicating that the defibrillator applied a defibrillation shock to a patient at an emergency scene at a time after the patient's arrival at the emergency room was logged according to the reference clock.

The probability that incongruous results will occur increases as the number of first responders and emergency care providers continues to grow. The worsening of the time-reporting aspect of a medical emergency may result from the failure of a care provider to use a reference clock, the care provider's use of unsynchronized clocks, or haphazard data logging techniques. Moreover, local protocols may not be in place to ensure clock synchronization to a reference time standard. As a result, incongruous time stamps are often placed on event data recorded by different organizations, precluding meaningful emergency event reconstruction and analysis.

SUMMARY OF THE INVENTION

In accordance with this invention, a system and method for synchronizing a clock in an electronic physiological instrument with a remote time base are provided. The electronic physiological instrument records medical event data and electronically associates time stamps with the event data. During the recordation or after the recordation of the medical event data, the electronic physiological instrument is placed in communication with the remote time base. The remote time base initially determines a reference time from a master clock. The remote time base also transmits a request to the electronic physiological instrument for a current time from a clock in the electronic physiological instrument. If a response is received within a first time period, a time difference is determined between the reference time and the time transmitted from the electronic physiological instrument by subtracting the two times. The time difference is then electronically associated with the medical event data that is downloaded from the electronic physiological instrument. Associating the time difference with the medical event data allows the time stamps in the event data to be corrected to provide meaningful event reconstruction and analysis independent of any time differences between the two clocks and any time delays incurred in receiving the event data from the physiological instrument over the data connection.

In accordance with one aspect of the invention, the time difference is transmitted to the electronic physiological instrument to allow the clock of the electronic physiological instrument to be updated with the time difference. Updating the clock in the electronic physiological instrument ensures that the time stamps applied to subsequent medical event data are consistent with the master clock of the remote time base.

In accordance with another aspect of the invention, if a response is not received from the electronic physiological instrument within the first time period, the electronic physiological instrument clock is not synchronized with the master clock in the remote time base.

In accordance with still another aspect of the invention, the electronic physiological instrument and the reference time base are in data communication via a communication link such as a cellular link, a modem link, a radiofrequency link, an optical link, or a direct connection. The communications link allows transmission of event data and synchronization of the electronic physiological instrument clock with the master clock of the reference time base to be performed while the electronic physiological instrument is being used in the field.

It will be appreciated that several advantages arise from synchronizing the clock in the electronic physiological instrument with the master clock of the reference time base. Perhaps most importantly, the system and method for synchronizing the clock permit post-event reconstruction and analysis to be meaningful and accurate. Because the synchronization automatically occurs when event data is being downloaded from the electronic physiological instrument, the need to rely on adherence to local protocols to synchronize device clocks with the master clock of the reference time base in the local emergency medical organization is removed.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein:

FIGS. 4A, 4B, and 4C are flowcharts of an alternate method for correcting time stamps made by a clock in an electronic physiological instrument according to the present invention;

FIG. 6 is a block diagram of a network of an electronic physiological instrument and remote time bases according to the present invention.

DETAILED DESCRIPTION OF THE PREFERRED EMBODIMENT

Figure 1A:
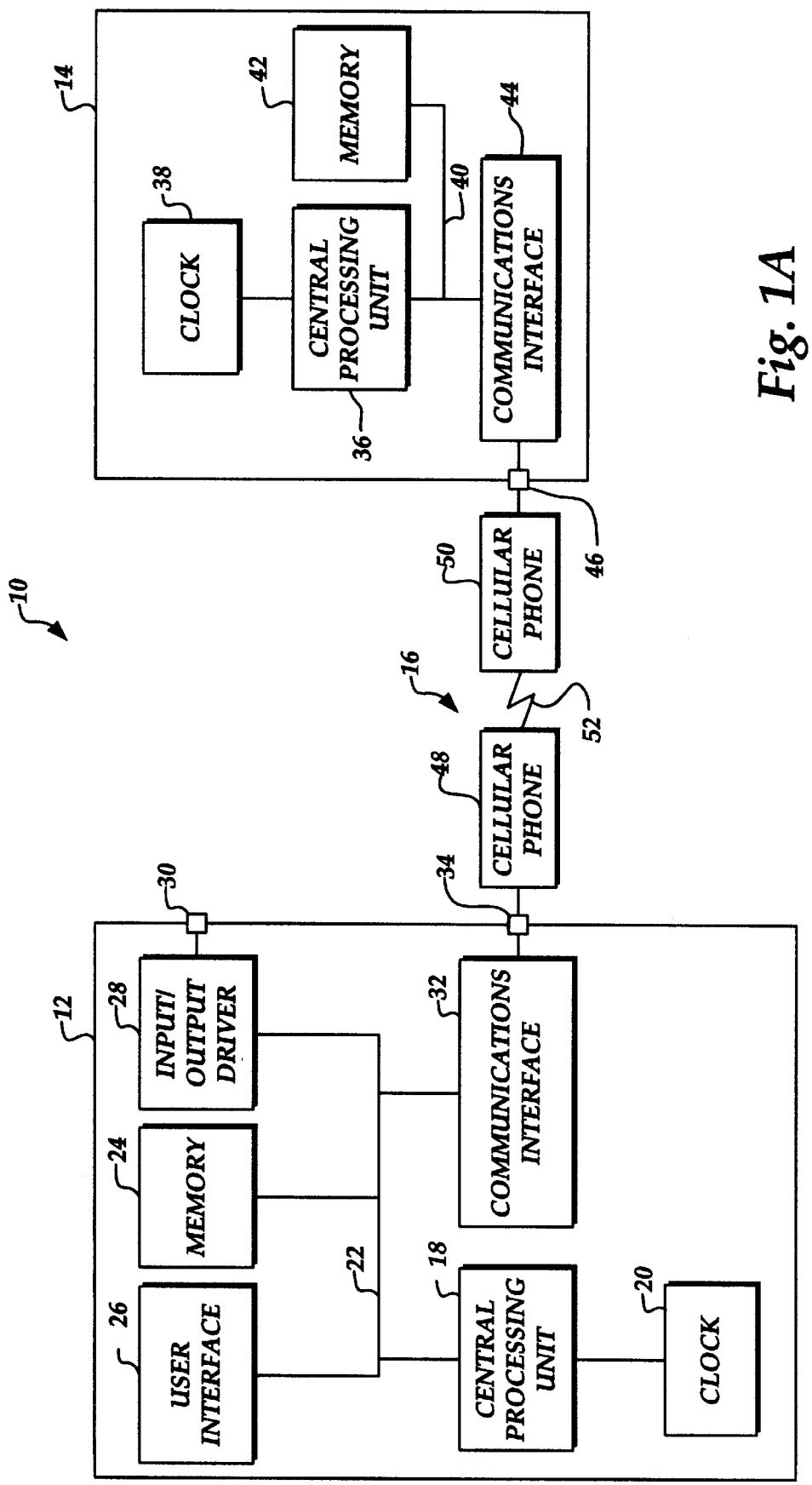
FIG. 1A is a block diagram of a system for synchronizing a clock in an electronic physiological instrument with a reference time base according to an embodiment of the present invention.

FIG. 1A is a block diagram of a system 10 for synchronizing a clock in an electronic physiological instrument with a remote time base 14. The electronic physiological instrument is preferably a portable defibrillator/monitor 12. Defibrillator/monitors are among the first devices to be attached to patients in cardiorespiratory emergencies, and their wide use makes them well suited for storing additional incident information. Further, because many emergency medical organizations transmit recorded medical emergency event information to a central office for later clinical review, the system of the present invention for synchronizing a clock with a remote time base is especially well suited to defibrillator/monitors. For example, the LIFEPAK® 500, manufactured and sold by Physio-Control Corporation of Redmond, Washington, stores time-stamped messages in an event log corresponding to events and procedures performed at the scene of an emergency. Software, such as the QUICK-VIEW™ 500 data management system by Physio-Control Corporation, can reconstruct the incident time line from this information and provide a concise summary of medical emergency events.

The system 10 includes a data communication link 16 that connects the defibrillator/monitor 12 with the remote time base 14. As will be described in detail below, the remote time base 14 receives a system time from the defibrillator/monitor 12 over the data communication link 16, generates a time correction, and transmits the time correction to the defibrillator/monitor 12 via the data communication link 16.

The defibrillator/monitor 12 includes a central processing unit 18, a memory 24, a user interface 26, an input/output driver 28, a communications interface 32, and a communications port 34, all connected by a common bus 22. The central processing unit 18 is further connected to a defibrillator/monitor clock 20, and the input/output driver 28 is connected to a therapy port 30. Defibrillator/monitors 12 are well known in the art of electronic physiological instruments. Thus, details of the defibrillator/monitor's construction and operation are not discussed in detail below and are not necessary for an understanding of the invention.

The defibrillator/monitor clock 20 is used by the central processing unit 18 to time stamp recorded data. The central processing unit 18 collects event data via the therapy port 30 and the input/output driver 28. Suitable data gathering sensors and devices for delivering medical therapy, such as defibrillator electrodes, may be connected to the therapy port 30. The event data is suitably formatted, for example in the preferred embodiment, according to the CODE SUMMARY™ standard adopted by Physio-Control Corporation of Redmond, Wash., in its line of portable defibrillators, monitors, and pacers. The central processing unit 18 places electronic time stamps on the event data, and stores the event data and time stamps in the memory 24. The memory 24 includes a portion of nonvolatile memory that maintains the event data and time stamps stored in the memory 24 even if power to the defibrillator/monitor 12 fails.

The communications interface 32 couples the central processing unit 18 and the memory 24 to the communications port 34. The communications interface 32 suitably includes a universal asynchronous receiver/transmitter (UART) that converts parallel data from the common bus 22 to serial data for transmission purposes. The communications interface 32 also includes a serial data driver, such as an RS-232 driver, for connection of the defibrillator/monitor to a peripheral device.

The remote time base 14 is preferably a computer, such as a personal computer used in a central office of an emergency medical organization. The remote time base 14 includes a central processing unit 36, a memory 42, and a communications interface 44 linked by a common bus 40. The central processing unit 36 is connected to a master clock 38. The memory 42 may be any number of acceptable volatile memories (such as RAM) or nonvolatile memories (such as hard disk, floppy disk, ROM, EEPROM, etc.) suitable for storing event data. However, the memory 42 preferably includes a portion of nonvolatile memory to retain information, such as time-stamped event data, stored in the memory 42 after power is removed from the remote time base 14. The communications interface 44 is coupled to a communications port 46. Preferably, the communications interface 44 is a modem to transmit and receive serial communications to and from the defibrillator/monitor 12. Because computers are known in the art, the additional details of the remote time base 14 will not be discussed.

Figure 1B:
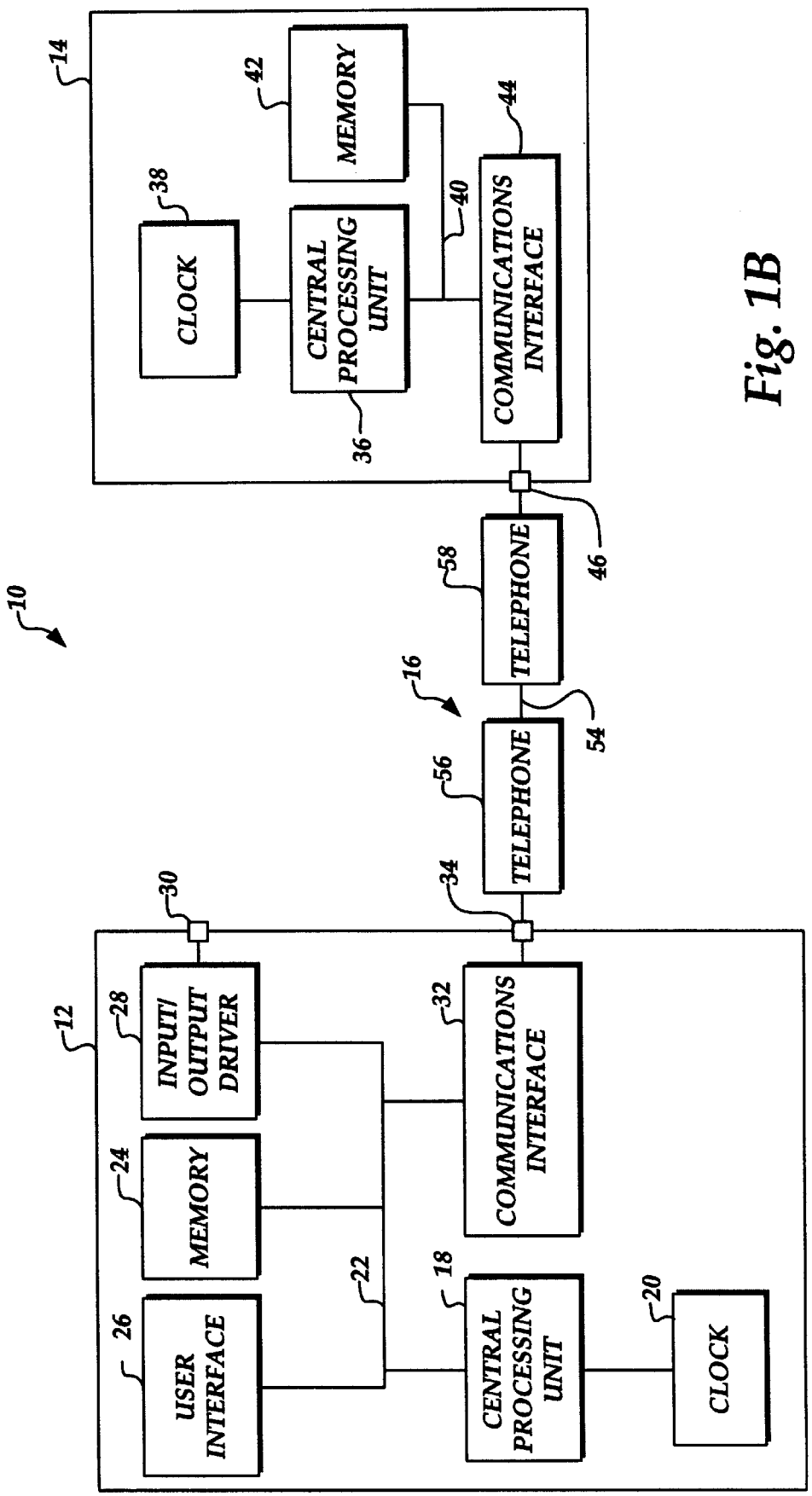
FIGS. 1B and 1C are block diagrams of systems for synchronizing a clock in an electronic physiological instrument with a reference time base according to other embodiments of the present invention.
Figure 1C:
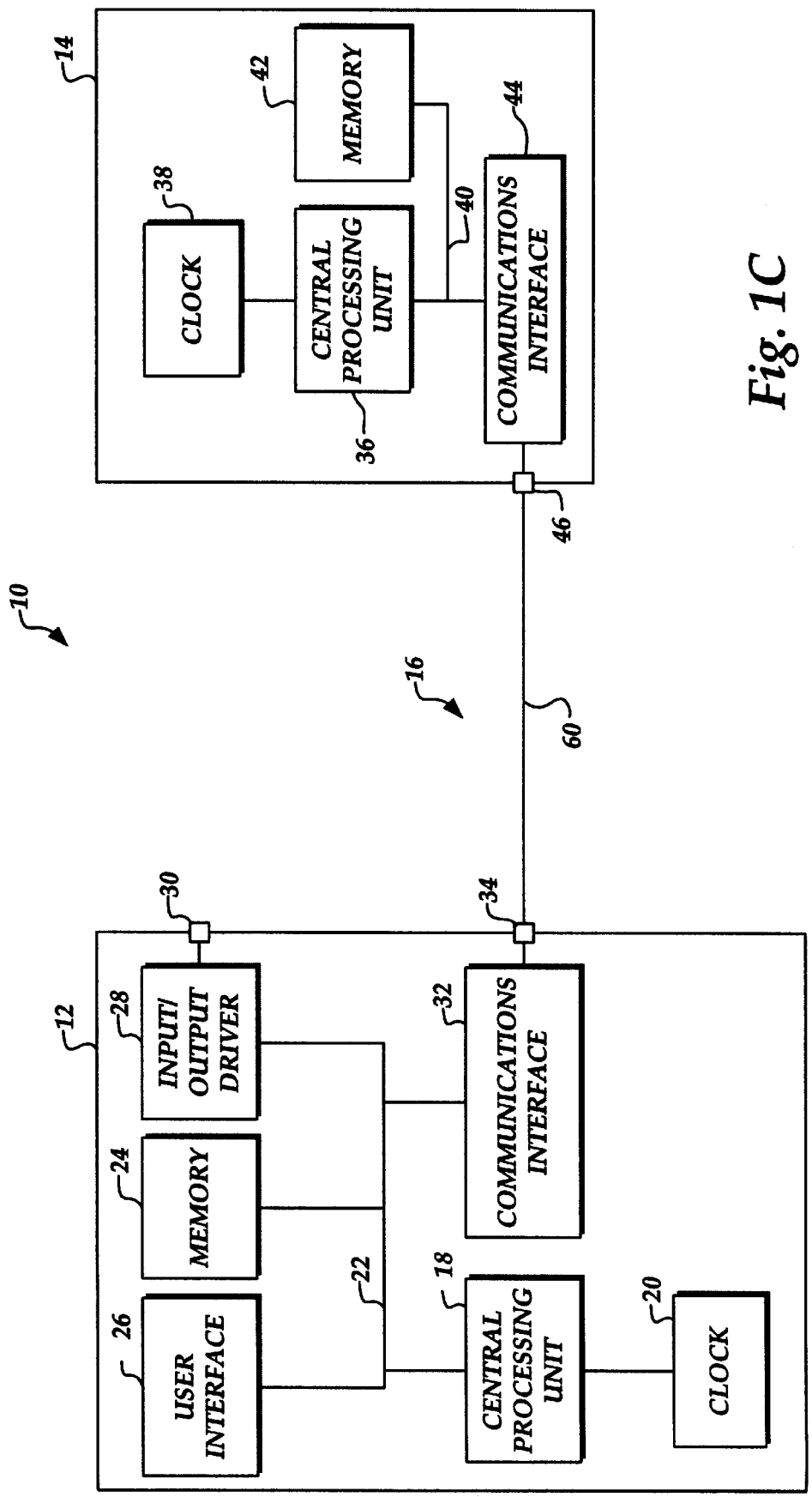

In one preferred embodiment of the invention, the data communication link 16 is a cellular data communication link. The data communication link 16 includes a first cellular phone 48 electrically connected to the communications port 34 of the defibrillator/monitor 12, and a second cellular phone 50 electrically connected to the communications port 46 of the remote time base 14. The first and second cellular phones 48 and 50 are in cellular communication via a cellular connection 52. A cellular communication link allows the defibrillator/monitor 12 to transmit event data to the remote time base 14 during a medical emergency, or soon after the emergency while the defibrillator is still in the field. Referring now to FIG. 1B, in another preferred embodiment of the invention the defibrillator/monitor 12 and the remote time base 14 are connected by a phone line 54 instead of a cellular communication link. In this embodiment, the communication ports 34 and 46 are connected to a phone system, such as a Public Telephone System Network, via suitable telephones 56 and 58, respectively. Referring now to FIG. 1C, in another preferred embodiment of the invention the defibrillator/monitor 12 and the remote time base 14 are directly connected via a cable 60, such as an electrical or optical cable, coupled between the communication ports 34 and 46. It will be appreciated that the data communications link 16 suitably includes other links such as, without limitation, a radiofrequency (RF) link and an infrared (IR) link. It will further be appreciated that the above examples of the communications link are given by way of non-limiting example and are not intended to limit the scope of the invention.

Figure 2A:
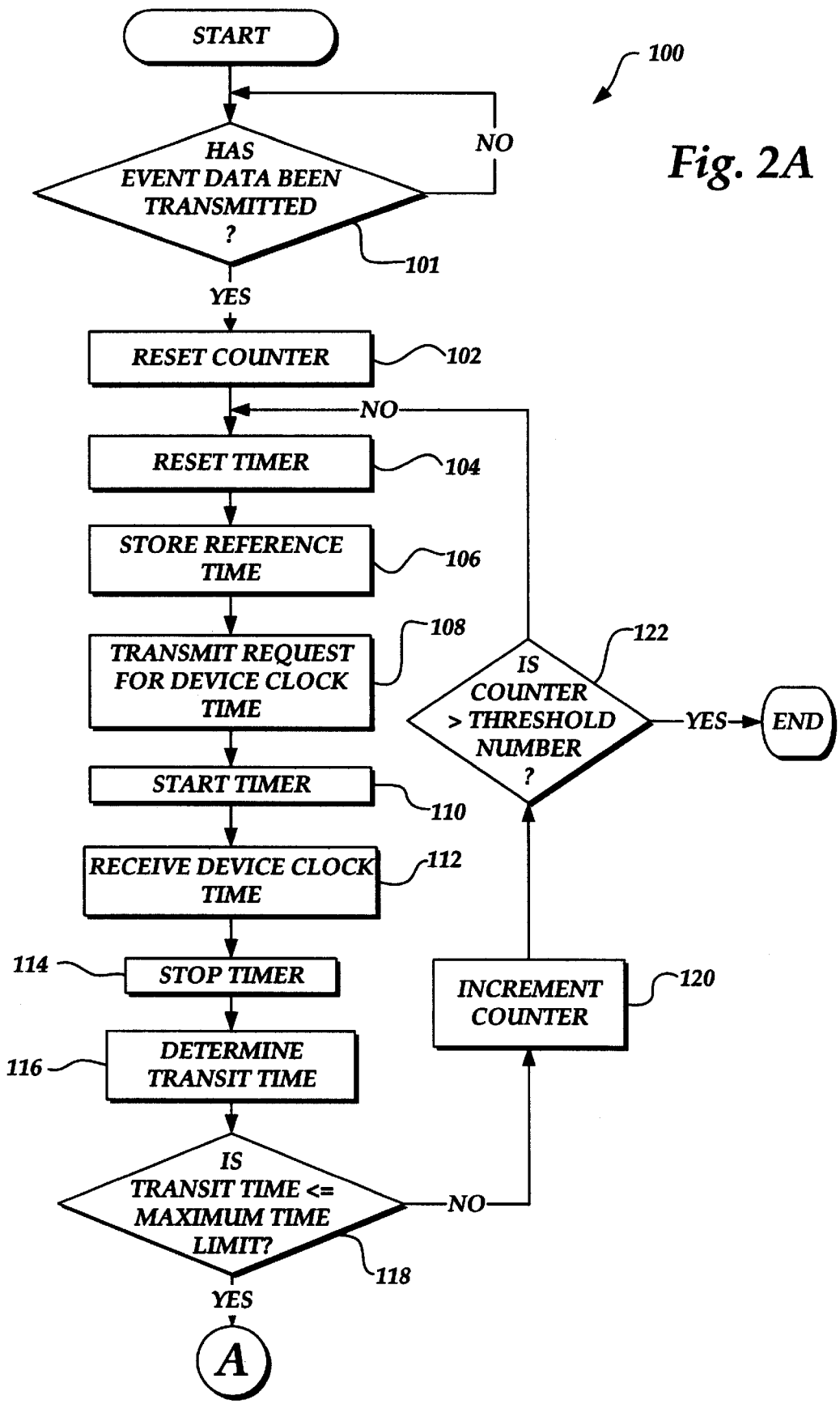
FIGS. 2A and 2B are flowcharts of a method for correcting time stamps made by a clock in an electronic physiological instrument according to the present invention.
Figure 2B:
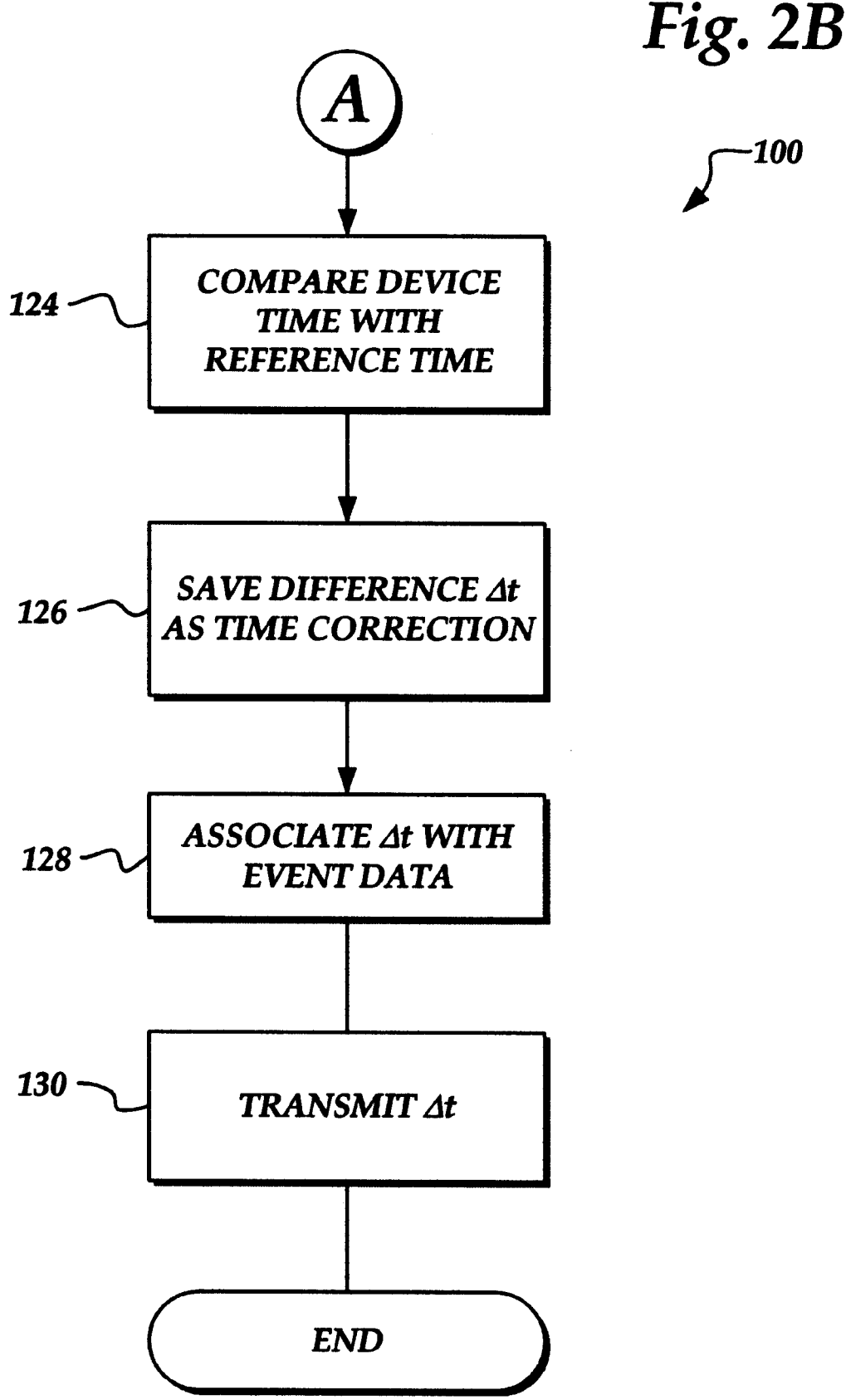

A preferred software routine 100 that is resident in the remote time base 14 and used to correct time stamps received from the defibrillator/monitor 12 so that they reflect the accurate time maintained by the master clock 38 of the remote time base 14 is shown in FIGS. 2A and 2B. The preferred software routine 100 is stored in the memory 42 and performed by the central processing unit 36 of the remote time base 14. As depicted in FIG. 2A, the preferred software routine 100 begins when initiated by a start command. In a preferred embodiment, the software routine 100 is automatically initiated immediately following the transmittal of event data from the defibrillator/monitor 12 to the remote time base 14 as determined at a decision block 101. Automatic initiation of the routine 100 is desirable after the event data is received over the cellular data communication link 16, since it ensures that the defibrillator/monitor clock 20 will be frequently synchronized with the master clock 38 while the defibrillator/monitor 12 is in use. Automatic initiation also synchronizes the defibrillator/monitor clock 20 without reliance upon an operator remembering to perform the synchronization. The preferred software routine may also, however, be manually initiated from either the defibrillator/monitor 12 or the remote time base 14.

Immediately after the software routine 100 is initiated, a counter is reset at a block 102 and a timer is reset at a block 104. The counter and the timer are both suitably implemented in software. A reference time is stored in the memory 42 of the remote time base 14 at a block 106. The reference time is the current time as determined from the master clock 38 of the remote time base 14.

At a block 108, the remote time base 14 transmits a request over the data communication link 16 for the current time indicated by the defibrillator/monitor clock 20. When the request for the current time is sent, the software timer implemented by the remote time base 14 is started at a block 110. The timer is used to determine a time interval required for the defibrillator/monitor 12 to respond to the request.

Because of possible delays that may be experienced over the data communications link 16, such as, for example, delays caused by noise, a maximum time limit is established for the defibrillator/monitor 12 to respond with the current time from the defibrillator/monitor clock 20. During transmission, especially cellular transmission, delays in the communication may occur as the communication interfaces 32 and 44 adjust data transmission parameters to transmit packets of data over the data communications link 16. Setting a maximum time limit for response ensures that the response containing the current time of the defibrillator/monitor clock 20 is received within a maximum time limit from the request from the remote time base 14. If excessive delays occur, then the reported time of the defibrillator/monitor clock 20 will not be accurate. In such a case, synchronizing the defibrillator/monitor clock 20 is not desirable.

A response containing the current time of the defibrillator/monitor clock 20 is received by the remote time base 14 at a block 112. The defibrillator/monitor clock 20 time is stored in the memory 42 of the remote time base 14. When the response containing the defibrillator/monitor clock 20 is received, the software timer is stopped at a block 114.

The transit time of the data communication link 16 is determined at a block 116 by subtracting the starting time of the timer at block 110 from the stopping time of the timer at block 114. The time difference represents the time for the request for the defibrillator/monitor clock 20 time to be transmitted from the remote time base 14 over the data communication link 16 to the defibrillator/monitor 12, for the defibrillator/monitor 12 to determine the current time of the defibrillator/monitor clock 20, and for the defibrillator/monitor 12 to transmit a response to the remote time base 14 via the data communication link 16.

At a decision block 118, a determination is made of whether the transit time is less than or equal to the maximum time limit. The maximum time limit is acceptably between approximately 1 and 60 seconds, is suitably between approximately 5 and 10 seconds, and is preferably approximately 5 seconds. Such a maximum time limit provides sufficient time for the defibrillator/monitor 12 to receive the request for the defibrillator/monitor clock 20 time and to transmit the time to the remote time base 14. A transit time greater than the maximum time limit may indicate that a problem exists in the data connection between the defibrillator/monitor 12 and the remote time base 14. A problem internal to the defibrillator/monitor 12 or the remote time base 14 can also cause the transit time to be greater than the maximum time limit. Because it may be difficult to determine the cause of the delay, it is desirable to synchronize the defibrillator/monitor clock 20 with the master clock 38 only when the transit time is determined to be less than the maximum time limit.

When a determination is made that the transit time is greater than the maximum time limit at decision block 118, the counter is incremented by one at a block 120. A determination is made at a decision block 122 of whether the counter indicates a number that is greater than a threshold number. The threshold number represents the number of requests for the defibrillator/monitor clock 20 time within the maximum time limit. The threshold number is suitably between ten and thirty, and is preferably ten, to limit the number of requests in the event of a problem in establishing a connection. If a determination is made at the decision block 122 that the counter is greater than the threshold number, then the software routine 100 ends and no further action is taken. If a determination is made at the decision block 122 that the counter is less than or equal to the threshold number, then the software routine returns to the block 104 and another request is made of the defibrillator/monitor clock 20 time.

Referring now to FIG. 2B, if the response from the defibrillator/monitor 12 is received within the maximum time limit, the software routine 100 continues to a block 124 where a comparison is made of the current defibrillator/monitor clock 20 time and the reference time determined from the master clock 38. The difference between the defibrillator/monitor clock 20 time and the reference time is saved in memory as a time difference Δt at a block 126. The time difference Δt is a time correction for updating event data time stamps and for updating the defibrillator/monitor clock 20. At a block 128, the central processing unit 36 associates the time difference Δt with the event data that has been previously transmitted from the defibrillator/monitor 12 and stored in the memory 42. At a block 130, the time difference Δt is also transmitted to the defibrillator/monitor 12 via the data communication link 16. The time difference Δt, rather than the reference time, is used as a time correction because the time difference Δt is independent of any time delays introduced in the requests for the defibrillator/monitor clock 20 time update via the data communication link 16.

Figure 3:
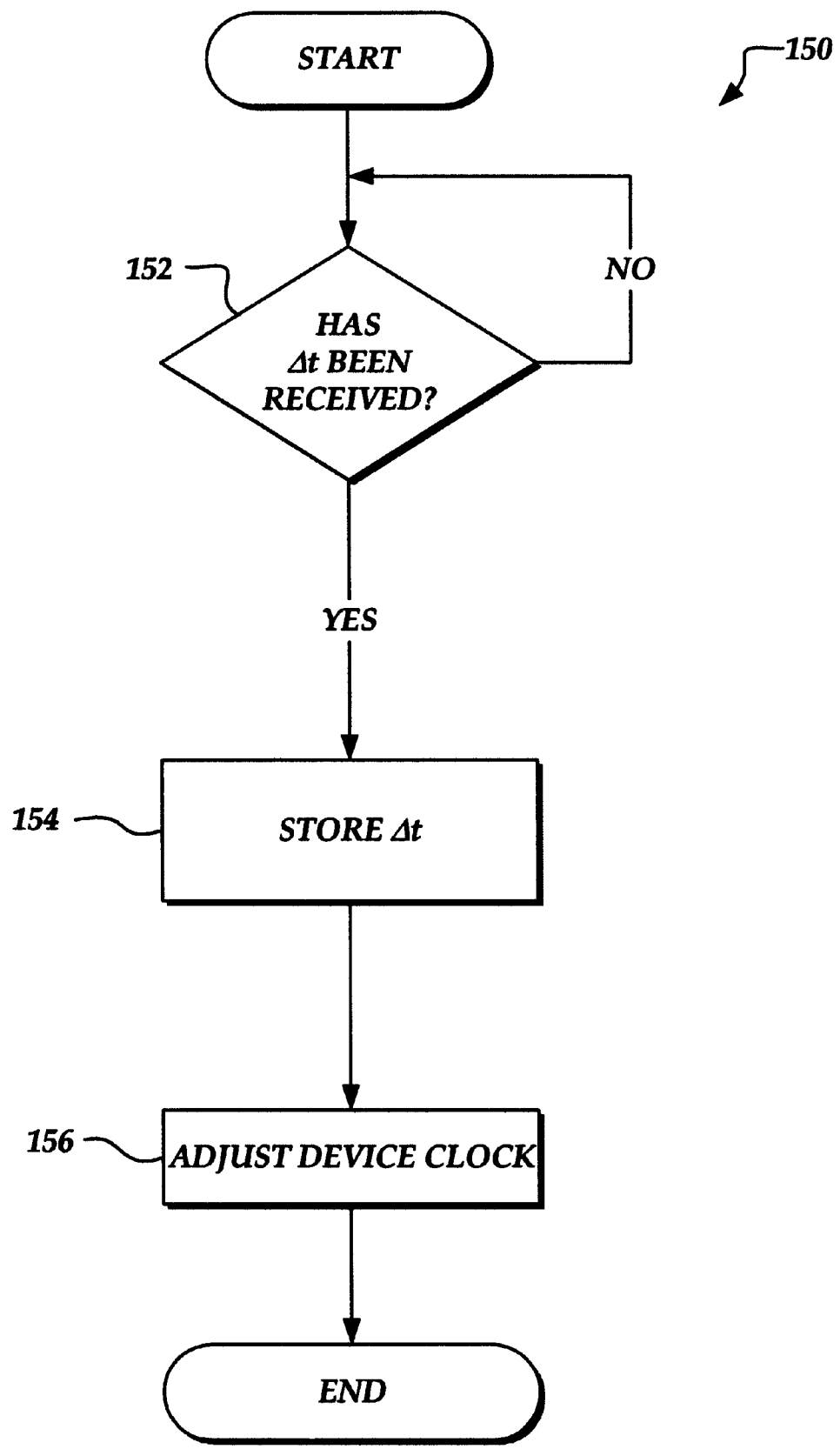
FIG. 3 is a flowchart of a method for synchronizing a clock in an electronic physiological instrument with a reference time base according to the present invention.

Referring now to FIG. 3, a preferred software routine 150 that is resident in the defibrillator/monitor 12 is shown for synchronizing the defibrillator/monitor clock 20 with the master clock 38 of the remote time base 14. The software routine 150 is stored in the memory 24 and performed by the central processing unit 18 of the defibrillator/monitor 12. At a decision block 152 a determination is made whether the time difference Δt has been received by the defibrillator/monitor 12 via the data communication link 16. At a block 154, the time difference Δt is stored in the memory 24. When the remote time base 14 is a central computer for an emergency medical system, the time difference Δt can be used to synchronize to the reference time of the emergency medical organization independent of the communication delay between the defibrillator/monitor 12 and the remote time base 14.

At a block 156, the central processing unit 18 applies the time difference -t to adjust the defibrillator/monitor clock 20. As noted above, adjusting the defibrillator/monitor clock 20 by the time difference Δt is preferred over setting the defibrillator/monitor clock 20 to the reference time because the time difference Δt is independent of the communication delay.

Figure 4B:
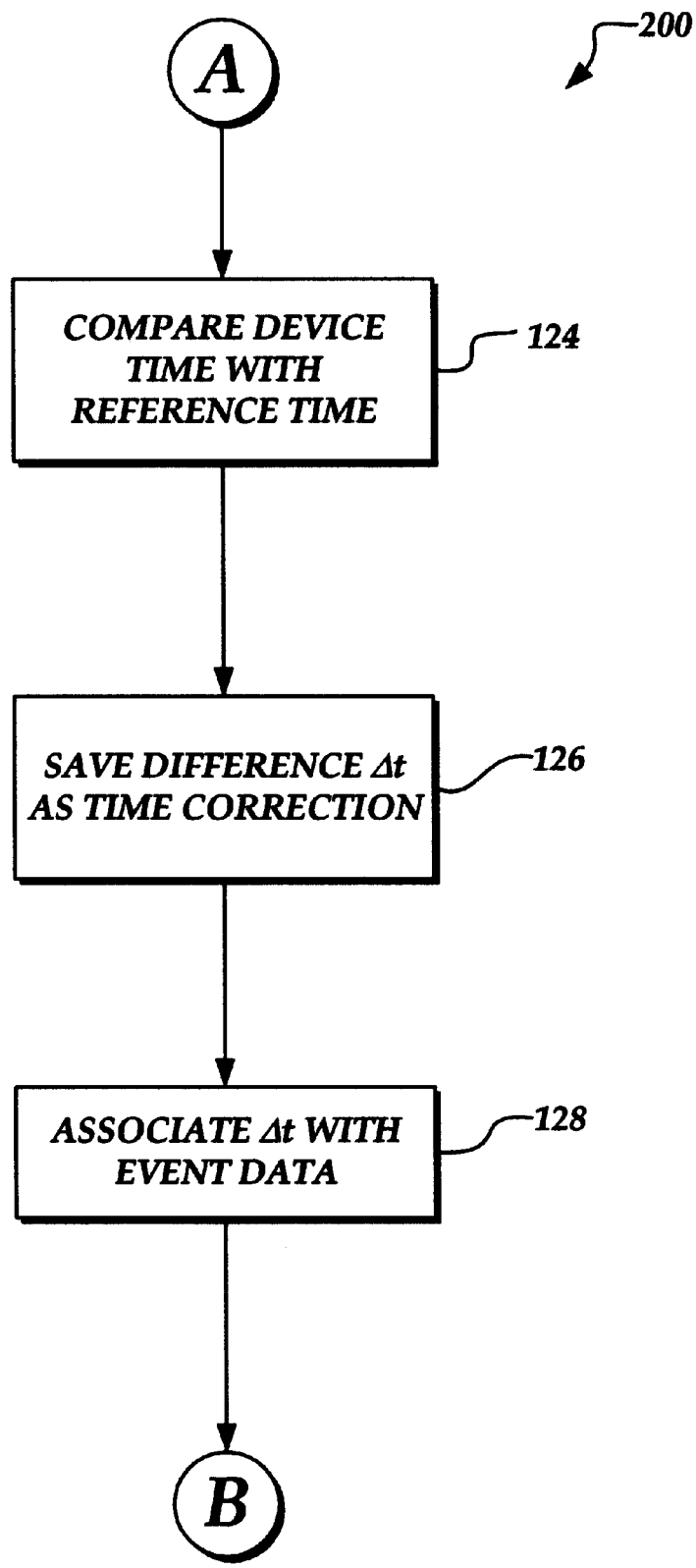
Figure 4C:
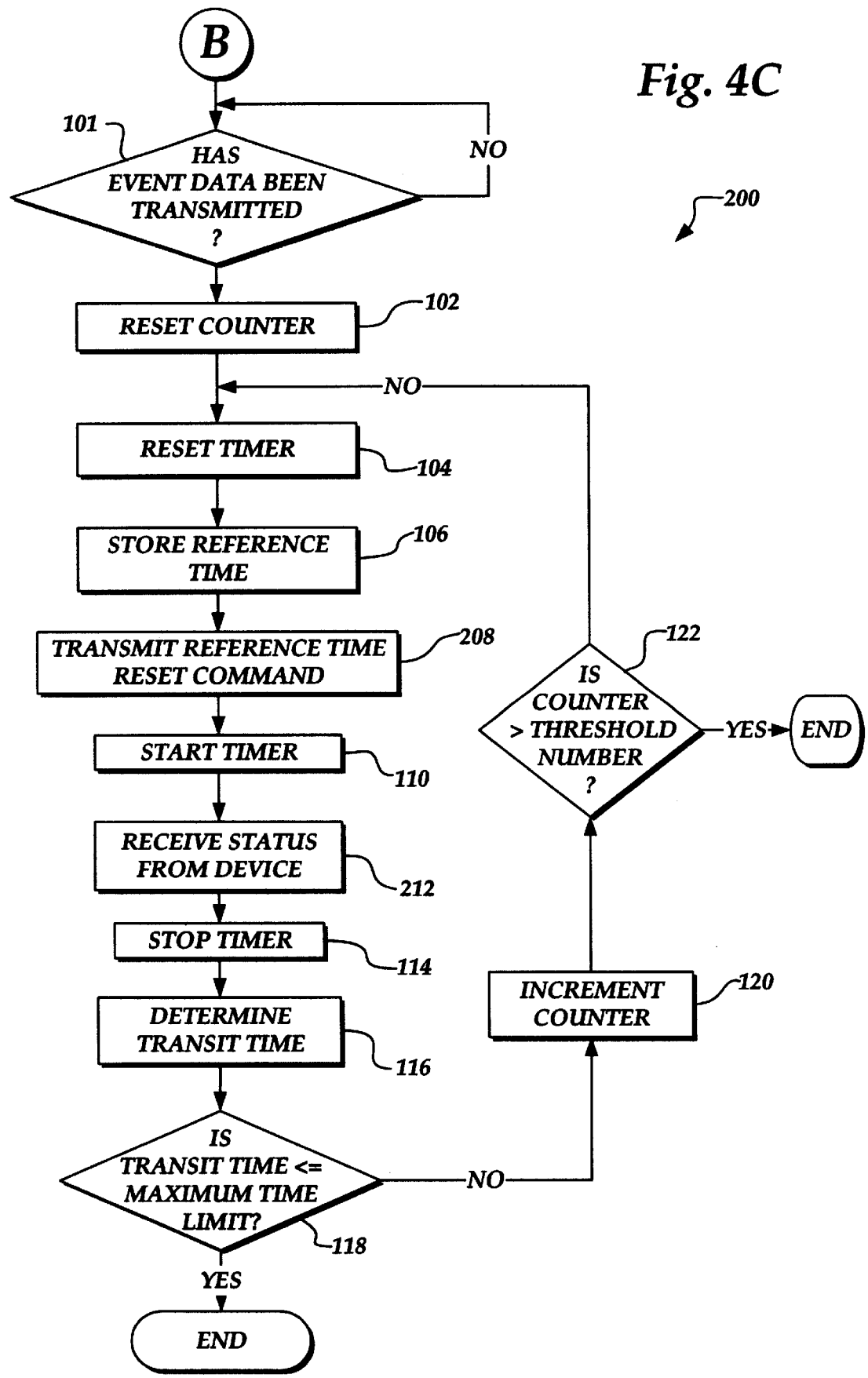

An alternative software routine 200 that is resident in the remote time base 14 and used to adjust the time stamps received with the event data transmitted by the defibrillator/monitor 12 so that the time stamps correspond to the time maintained by the master clock 38 in the remote time base 14 is provided in FIGS. 4A through 4C. The alternative software routine 200 is suitably stored in the memory 42 of the remote time base 14 and performed by the central processing unit 36. As will be described below, the alternative software routine 200 adjusts the time stamps made by the defibrillator/monitor 12 in a similar manner to the preferred software routine 100. However, the alternative software routine corrects the defibrillator/monitor clock 20 with the reference time provided by the remote time base 14 rather than using the time difference Δt.

As seen in FIG. 4A, the alternative software routine 200 performs the steps 102 through 122 as discussed above for the preferred software routine 100. The alternative software routine varies, however, from the preferred software routine in that the maximum time limit used in the alternative software routine 200 is shorter than the maximum time limit used in the preferred software routine 100. The maximum time limit for response is suitably approximately 5 seconds and is preferably approximately 2 seconds for the alternative software routine 200. The maximum time limit is reduced to minimize the error in the time that is downloaded to the defibrillator/monitor clock 20.

When the transit time is less than the maximum time limit at decision block 118, the alternative software routine 200 continues as shown in FIG. 4B. The alternative software routine 200 performs the blocks 124, 126, and 128 as described above. That is, the alternative software routine determines the time difference Δt, stores the time difference Δt in the memory 42 of the remote time base 14 as a time correction, and associates the time difference Δt with the event data previously downloaded from the defibrillator/monitor 12 and stored in the memory 42 of the remote time base 14.

The alternative software routine continues as shown in FIG. 4C. The alternative software routine repeats the blocks 101, 102, 104, and 106 resetting the counter, the timer, and storing the reference time. At a block 208, the reference time and a command to reset the defibrillator/monitor clock 20 to the reference time are transmitted to the defibrillator/monitor 12. At a block 110 the timer is started. At a block 212, the remote time base 14 receives a status acknowledgment from the defibrillator/monitor 12 that the defibrillator has reset the defibrillator/monitor clock 20 to the reference time. At the block 114 the timer is stopped when the status acknowledgment has been received from the defibrillator/monitor 12. At block 116, the transit time is determined, that is, the time that it takes the command to write the reference time to the defibrillator/monitor clock 20 to be transmitted, performed, and acknowledged. The alternative software routine repeats the blocks 118–122, using the shortened maximum time limit as discussed above.

Figure 5:
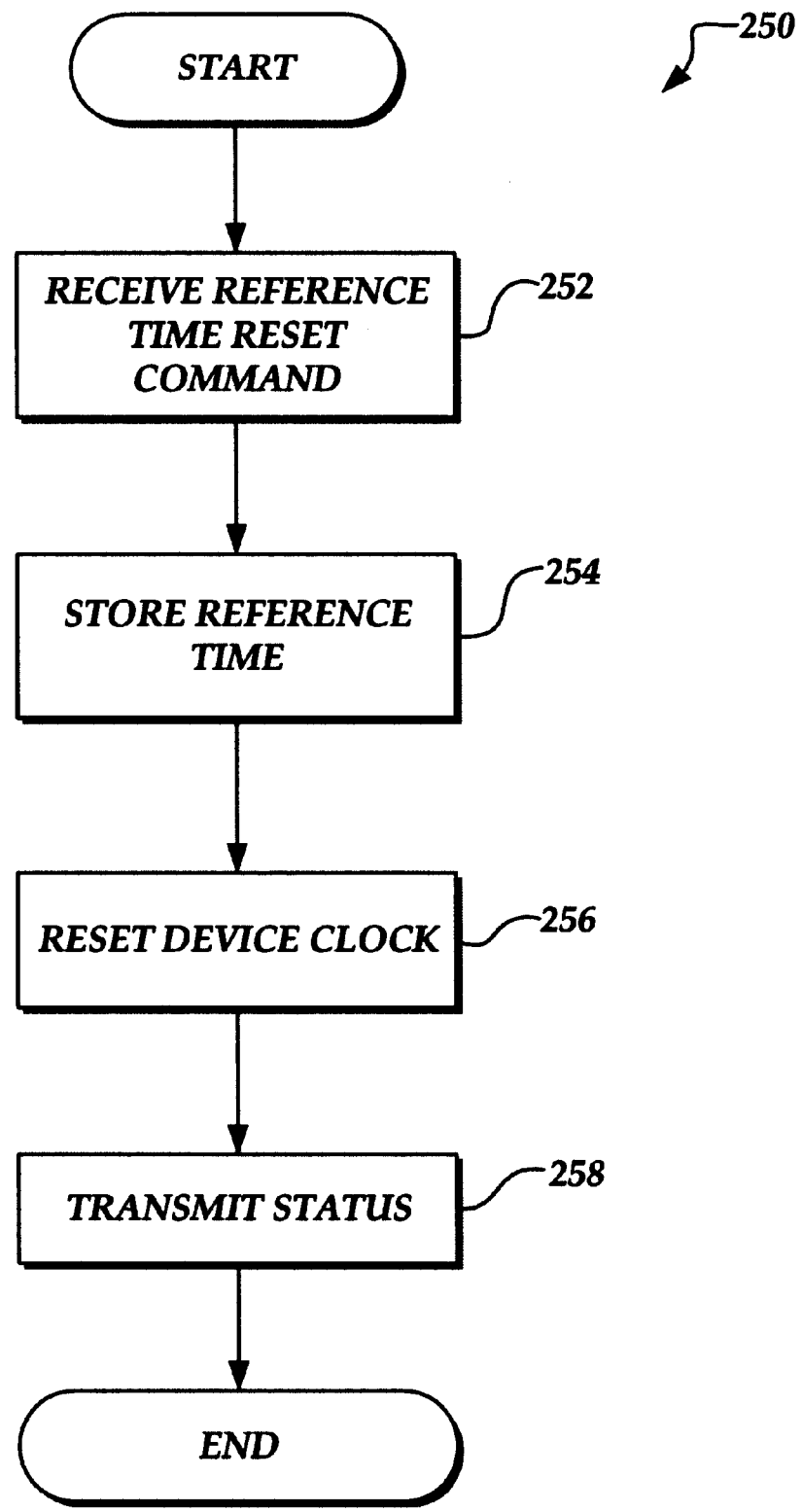
FIG. 5 is a flowchart of an alternate method for synchronizing a clock in an electronic physiological instrument with a master clock in a reference time base according to the present invention.

FIG. 5 shows an alternative software routine 250 resident in the defibrillator/monitor 12 for synchronizing the defibrillator/monitor clock 20 with the master clock 38 of the remote time base 14 by writing the reference time to the defibrillator/monitor clock 20. The alternative software routine 250 is stored in the memory 24 and performed by the central processing unit 18 of the defibrillator/monitor 12. The alternative software routine 250 uses the reference time to update the defibrillator/monitor clock 20 and thus may be less accurate than the preferred embodiment because it is subject to communication delays.

At a block 252 the defibrillator/monitor 12 receives the reference time and the command to reset the defibrillator/monitor clock 20. At a block 254, the reference time is stored in the memory 24. At a block 256, the defibrillator/monitor clock 20 is reset so that the defibrillator/monitor clock time equals the reference time. At a block 258, the defibrillator/monitor 12 transmits a message to the remote time base 14 indicating that the defibrillator/monitor clock 20 has been reset to the reference time.

FIG. 6 is a block diagram of a network 300 of an electronic physiological instrument and remote time bases according to the present invention. The network 300 includes an electronic physiological instrument such as a defibrillator/monitor 312 as described above, a plurality of remote time bases 314, 315, and 317 such as the computer described above, and a plurality of data communication links 316 such as the data communication link 16 as described above. The remote time bases 314, 315, and 317 may be used throughout an emergency medical organization. For example, the remote time base 314 may be in a fire station, the remote time base 315 may be in a hospital, and the remote time base 317 may be in a central dispatching office. Preferably, the central dispatch office remote time base 317 is used as a master remote time base. The defibrillator/monitor 312 is equipped as described above and is provided with either the preferred software routine 150 or the alternative software routine 250. Each of the remote time bases 314, 315, and 317 is equipped as above and is provided with either the preferred software routine 100 or the alternative software routine 200.

When data is transmitted from the defibrillator/monitor 312 to the remote time base 314, the remote time base 314 queries and sets the clock of the defibrillator/monitor 312. When the remote time base 314 sends to the remote time base 315, the remote time base 315 queries and sets the clock of the remote time base 314. When the remote time base 315 sends to the remote time base 317, the remote time base 317 queries and sets the clock of the remote time base 315.

While the preferred embodiment of the invention has been illustrated and described, it will be apparent that various changes can be made therein without departing from the spirit and scope of the invention.

The embodiments of the invention in which an exclusive property or privilege is claimed are defined as follows:

1. A method for adjusting time associated with medical event data taken by an electronic physiological instrument, the method comprising:

using the electronic physiological instrument to record the medical event data and electronically associate time with the medical event data;

connecting the electronic physiological instrument in data communication with a remote time base;

determining a reference time using the remote time base;

passing time data over the data connection between the remote time base and the electronic physiological instrument;

determining a time difference between the reference time and a time data indicated by a clock of the electronic physiological instrument;

electronically associating the time difference with the medical event data; and determining whether the time data indicated by a clock of the electronic physiological instrument is received within a first time period from determining the reference time when the time data is received within the first time period.

2. The method of claim 1, further comprising:

when the time data is not received within the first time period, repeating until a number of attempts reaches a threshold number:

determining the reference time;

receiving the time indicated by the clock of the electronic physiological instrument; and determining whether the time indicated by the clock of the electronic physiological instrument is received within the first time period.

3. The method of claim 2, further comprising associating the time difference with the medical event data using the remote time base.

4. The method of claim 2, wherein the first time period is approximately five seconds.

5. A method for adjusting time associated with medical event data taken by an electronic physiological instrument, the method comprising:

using the electronic physiological instrument to record the medical event data and electronically associate time with the medical event data;

connecting the electronic physiological instrument in data communication with a remote time base;

determining a reference time using the remote time base;

passing time data over the data connection between the remote time base and the electronic physiological instrument;

determining a time difference between the reference time and a time data indicated by a clock of the electronic physiological instrument;

electronically associating the time difference with the medical event data; and adjusting the clock of the electronic physiological instrument using the time difference.

6. The method of claim 5, further comprising:

starting a transit timer from a transit start time when transmission of the request for the time data begins; and stopping the transit timer at a transit stop time when the time data is received.

7. The method of claim 6, further comprising determining whether a difference between the transit start time and the transit stop time is less than the first time period.

8. The method of claim 5, wherein adjusting the clock of the electronic physiological instrument includes transmitting the time difference from the remote time base to the electronic physiological instrument.

9. A method for adjusting time associated with medical event data taken by an electronic physiological instrument, the method comprising:

using the electronic physiological instrument to record the medical event data and, electronically associate time with the medical event data;

connecting the electronic physiological instrument in data communication with a remote time base;

determining a reference time using the remote time base;

passing time data over the data connection between the remote time base and the electronic physiological instrument;

determining a time difference between the reference time and a time data indicated by a clock of the electronic physiological instrument;

electronically associating the time difference with the medical event data; and transmitting a request from the remote time base to the electronic physiological instrument for the time indicated by the clock of the electronic physiological instrument.

10. The method of claim 9, further comprising transmitting the time indicated by the clock of the electronic physiological instrument to the remote time base in response to the request.

11. A method for adjusting time associated with medical event data taken by an electronic physiological instrument, the method comprising:

using the electronic physiological instrument to record the medical event data and electronically associate time with the medical event data;

connecting the electronic physiological instrument in data communication with a remote time base;

determining a first reference time using the remote time base;

passing time data indicated by a clock of the electronic physiological instrument over a data connection;

determining whether the time data indicated by the clock of the electronic physiological instrument is received within a first time period from determining the first reference time;

determining a first time difference between the first reference time and the time data indicated by the clock of the electronic physiological instrument when the time data is received within the first time period;

electronically associating the first time difference with the medical event data;

determining a second reference time using the remote time base;

transmitting the second reference time from the remote time base to the electronic physiological instrument over the data connection;

determining whether the second reference time is received within the first time period from determining the second reference time; and adjusting the clock of the electronic physiological instrument using the second reference time when the second reference time is received within the first time period.

12. The method of claim 11, further comprising:

when the second reference time is not received within the first time period, repeating until a number of attempts reaches a threshold number:
  determining the second reference time;
  receiving the second reference time; and
  determining whether the second reference time is received within the first time period.

13. The method of claim 12, further comprising:

starting a transit timer from a transit start time when transmission of the second reference time begins;

stopping the transit timer at a transit stop time when the second reference time is received; and determining whether a difference between the transit start time and the transit stop time is less than the first time period.

14. The method of claim 13, wherein the first time period is approximately two seconds.

15. A system for adjusting time associated with medical event data, the system comprising an electronic physiological instrument including:
means for recording medical event data:
a first clock;
means for associating time data indicated by the first clock with the medical event data,
a first memory that stores the medical event data; and
a first communications interface for transferring data;
a data communications link in data communication with the first communications interface; and
a remote time base including:
a second clock;
means for determining a reference time from the second clock;
a second communications interface for transferring data, the second communications interface being in data communication with the data communications link;
means for determining a time difference between the reference time and the time data indicated by the first clock;

means for associating the time difference with the medical event data; and means for determining whether the time data indicated by the first clock is received within a first time period from determining the reference time.

16. The system of claim 15, wherein the second communications interface of the remote time base is configured to receive the time indicated by the first clock of the electronic physiological instrument and transmitted by the first communications interface of the electronic physiological instrument over the data communication link.

17. The system of claim 15, wherein the first communications interface of the electronic physiological instrument is configured to receive the time difference transmitted by the second communications interface of the remote time base over the data communications link.

18. The system of claim 15, wherein the electronic physiological instrument comprises a defibrillator.

19. The system of claim 15, wherein the remote time base comprises a computer.

20. The system of claim 15, wherein the predetermined time period comprises five seconds.

21. The system of claim 15, wherein the data communications link comprises a cellular link.

22. The system of claim 15, wherein the data communications link comprises a Public Telephone System Network.

23. The system of claim 15, wherein the data communications link comprises a cable.

24. The system of claim 23, wherein the cable comprises an electrical cable.

25. The system of claim 23, wherein the cable comprises an optical cable.

26. A system for adjusting time associated with medical event data, the system comprising:

an electronic physiological instrument including:
means for recording medical event data;
a first clock;
means for associating time data indicated by the first clock with the medical event data,
a first memory that stores the medical event data;
a first communications interface for transferring data; and
means for adjusting the time indicated by the first clock using a time difference between a reference time and the time data indicated by the first clock;
a data communications link in data communication with the first communications interface and
a remote time base including:
a second clock;
means for determining a reference time from the second clock;
a second communications interface for transferring data, the second communications interface being in data communication with the data communications link;
means for determining the time difference between the reference time and the time data indicated by the first clock; and
means for associating the time difference with the medical event data.

* * * * *

UNITED STATES PATENT AND TRADEMARK OFFICE
CERTIFICATE OF CORRECTION

PATENT NO. : 5,921,938
DATED : July 13, 1999
INVENTOR(S) : D.D. Aoyama et al.

It is certified that error appears in the above-identified patent and that said Letters Patent is hereby corrected as shown below:

| COLUMN | LINE | |
|---|---|---|
| [57] col. 2 | Abstract line 5 of text | "data While" should read --data. While-- |
| [56] col. 2 | Refs. Cited (Other Publs., item 4) | "Seiko Receptor" should read --SEIKO RECEPTOR-- |
| 9 (Claim 3, | 57 line 1) | "of claim 2," should read --of claim 1,-- |
| 9 (Claim 4, | 60 line 1) | "of claim 2," should read --of claim 1,-- |
| 10 (Claim 9, | 31 line 5) | After "and" delete "," |
| 11 (Claim 15, | 41 line 2) | After "comprising" insert --:-- |
| 11 (Claim 15, | 43 line 4) | After "data" delete ":" and insert therefor --;-- |
| 11 (Claim 15, | 46 line 7) | After "data" delete "," and insert therefor --;-- |

UNITED STATES PATENT AND TRADEMARK OFFICE
CERTIFICATE OF CORRECTION

PATENT NO. : 5,921,938
DATED : July 13, 1999
INVENTOR(S) : D.D. Aoyama et al.

It is certified that error appears in the above-identified patent and that said Letters Patent is hereby corrected as shown below:

| COLUMN | LINE | |
|---|---|---|
| 12 (Claim 26, | 40 line 7) | After "data" delete "," and insert therefor --;-- |
| 12 (Claim 26, | 47 line 14) | After "interface" insert --;-- |

Signed and Sealed this

Seventh Day of March, 2000

Attest:

Q. TODD DICKINSON

*Attesting Officer*    *Commissioner of Patents and Trademarks*

UNITED STATES PATENT AND TRADEMARK OFFICE
CERTIFICATE OF CORRECTION

PATENT NO. : 5,921,938
DATED : July 13, 1999
INVENTOR(S) : D.D. Aoyama, et al.

It is certified that error appears in the above-identified patent and that said Letters Patent is hereby corrected as shown below:

| COLUMN | LINE | |
|---|---|---|
| 9 (Claim 3, line 1) | 57 | "of claim 2," should read --of claim 1,-- |
| 9 (Claim 4, line 1) | 60 | "of claim 2," should read --of claim 1,-- |

Signed and Sealed this

Twenty-third Day of May, 2000

Attest:

Q. TODD DICKINSON

Attesting Officer     Director of Patents and Trademarks